US008377003B2

(12) United States Patent
Wagner

(10) Patent No.: US 8,377,003 B2
(45) Date of Patent: Feb. 19, 2013

(54) POWER INJECTOR WITH RAM RETRACTION

(75) Inventor: Gary S. Wagner, Independence, KY (US)

(73) Assignee: Mallinckrodt LLC, Hazelwood, MO (US)

( * ) Notice: Subject to any disclaimer, the term of this patent is extended or adjusted under 35 U.S.C. 154(b) by 185 days.

(21) Appl. No.: 12/742,934

(22) PCT Filed: Nov. 19, 2008

(86) PCT No.: PCT/US2008/084011
§ 371 (c)(1),
(2), (4) Date: May 14, 2010

(87) PCT Pub. No.: WO2009/067502
PCT Pub. Date: May 28, 2009

(65) Prior Publication Data
US 2010/0268075 A1 Oct. 21, 2010

Related U.S. Application Data

(60) Provisional application No. 60/989,135, filed on Nov. 20, 2007.

(51) Int. Cl.
*A61M 37/00* (2006.01)
(52) U.S. Cl. ........................ 604/155; 604/154
(58) Field of Classification Search .................. 604/154, 604/155
See application file for complete search history.

(56) References Cited

U.S. PATENT DOCUMENTS

| 6,004,285 | A | 12/1999 | Sugahara |
| 6,582,399 | B1 | 6/2003 | Smith et al. |
| 7,419,478 | B1 | 9/2008 | Reilly et al. |
| 7,465,290 | B2 | 12/2008 | Reilly |
| 7,540,856 | B2 | 6/2009 | Hitchins et al. |
| 7,666,169 | B2 | 2/2010 | Cowan et al. |
| 7,670,315 | B2 * | 3/2010 | Cowan et al. ............... 604/155 |
| 7,682,345 | B2 | 3/2010 | Savage |
| 2003/0018252 | A1 * | 1/2003 | Duchon et al. ............. 600/432 |
| 2004/0039368 | A1 | 2/2004 | Reilly et al. |
| 2004/0064041 | A1 | 4/2004 | Lazzaro et al. |
| 2005/0182371 | A1 | 8/2005 | Wagner et al. |
| 2006/0079765 | A1 | 4/2006 | Neer et al. |
| 2006/0079768 | A1 | 4/2006 | Small et al. |
| 2006/0106347 | A1 | 5/2006 | Fago et al. |
| 2006/0167415 | A1 * | 7/2006 | Nemoto ...................... 604/154 |

(Continued)

OTHER PUBLICATIONS

Stellant D Dual Syringe Medrad CT Injection System. Brochure. Medrad Inc. (2005 copyright—4 pages).

(Continued)

*Primary Examiner* — Victoria P Schumate
(74) *Attorney, Agent, or Firm* — Marsh, Fischmann & Breyfogle LLP

(57) ABSTRACT

Various embodiments of syringe plunger driver or ram retraction protocols for a power injector are disclosed. In a first ram retraction protocol (184*a*), a first ram may be partially retracted (232), followed by a full retraction of a second ram (234), followed by a completion of the retraction of the first ram (238). In a second ram retraction protocol (184*b*), a first ram may be partially retracted (252), followed by a partial retraction of a second ram (254), and sometime thereafter each of the first and second rams may be completely retracted (260, 262). In a third ram retraction protocol (184*c*), the first and second rams are simultaneously and partially retracted (272), and sometime thereafter each of the first and second rams are completely retracted (276). In a fourth ram retraction protocol (184*d*), the first and second rams are simultaneously and fully retracted (292) based upon a programmed input or the like.

19 Claims, 12 Drawing Sheets

U.S. PATENT DOCUMENTS

2006/0184122 A1* 8/2006 Nemoto ............... 604/154
2006/0184123 A1* 8/2006 Gillespie et al. ........... 604/155
2006/0184124 A1   8/2006 Cowan et al.
2007/0100282 A1   5/2007 Small et al.

OTHER PUBLICATIONS

Stellant CT Injection System Operation Manual Catalog # SOM 700 EN. Medrad Inc. (2004 copyright—100 pages).

Stellant CT Injection System Operation Manual. Medrad Inc. (2004 copyright—92 pages).

Sabo, Kristine, Medrad Launches New Standard in CT Injection Technology ( . . .). PR Newswire [online], [retrieved on Dec. 10, 2012]. Retrieved from the Internet <URL: http://www.thefreelibrary.com/_/preint/PrintArticle.aspx?id=131728531 (3 pages).

* cited by examiner

POWER INJECTOR WITH RAM RETRACTION

CROSS-REFERENCE TO RELATED APPLICATIONS

This patent application is a U.S. National Stage of PCT/US08/84011, filed Nov. 19, 2008, which claims priority to U.S. Provisional Patent Application Ser. No. 60/989,135, that is entitled "POWER INJECTOR WITH RAM RETRACTION," and that was filed on Nov. 20, 2007. Priority is claimed to each patent application set forth in this Cross-Reference to Related Applications section.

FIELD OF THE INVENTION

The present invention generally relates to the field of power injectors and, more particularly, to the manner in which each of its syringe drivers or rams are retracted.

BACKGROUND

Various medical procedures require that one or more fluids be injected into the patient. Medical imaging procedures oftentimes involve the injection of contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is appropriately interconnected with an appropriate syringe plunger driver that is incorporated into the powerhead, such that operation of the syringe plunger driver axially advances the associated syringe plunger. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Sometimes during contrast-enhanced imaging procedures, a dual-syringe power injector is used. One syringe may contain contrast media (e.g., iodine or gadolinium solutions) and the other syringe may contain a flushing solution (e.g., saline). In order to increase the likelihood that the contents of both syringes have been completely injected, the power injector may be configured to advance its rams far enough to slightly compress both syringe plungers into the end limits of the respective syringe barrels. If the residual compression force is high enough, it can hinder the manual removal of the syringes by the user, and whether the power injector is of a side load or a front load configuration. When hindered in this manner, users have been known to first manually retract both rams individually a slight amount to remove the compression forces, before disconnecting the syringes from the power injector.

Dual-syringe power injectors that incorporate an automatic ram retraction feature are also known. In one known configuration, the automatic ram retraction feature is configured to retract the rams sequentially. In this case, the user must wait for the first ram to be completely retracted and for the second ram to begin its retraction before the compression force has been removed from the both syringes. This wait period can typically be from 10 to 25 seconds. This waiting period is considered to be an annoyance by at least some users, as neither of the syringes is typically removed until both rams have been retracted to at least some degree in accordance with the foregoing.

SUMMARY

First and second aspects of the present invention are each embodied by a method of operation for a medical fluid delivery system that includes a power injector. This power injector includes a powerhead, first and second syringes, and first and second syringe plunger drivers. These first and second aspects will now be separately addressed.

The first aspect includes executing a programmed retraction sequence, which includes first, second, and third retractions. The first retraction includes retracting the first syringe plunger driver to a first intermediate position, where the first syringe plunger driver is then stopped. The second retraction includes retracting the second syringe plunger driver at least toward or in the direction of a second fully retracted position. The third retraction includes retracting the first syringe plunger driver from its first intermediate position to a first fully retracted position. The first aspect further includes removing the first and second syringes from the powerhead of the power injector.

The second aspect includes executing a programmed retraction sequence that is automatically initiated by a programmed input to the power injector, and that includes first and second retractions. The first and second retractions include retracting the first and second syringe plunger drivers, respectively, at least toward or in the direction of first and second fully retracted positions, respectively. These first and second retractions occur simultaneously. The second aspect further includes removing the first and second syringes from the powerhead of the power injector.

A third aspect of the present invention is embodied by a method of operation for a medical fluid delivery system that includes a power injector. A user is provided with a first option to enable an automatic initiation of a syringe plunger driver retraction protocol, as well as a second option to enable a manual initiation of this same syringe plunger driver retraction protocol. An injection protocol may be executed using the power injector. The syringe plunger driver retraction protocol will be initiated depending upon the selected option, and will then be executed.

The first and second options in accordance with the third aspect may be presented on one or more graphical user interfaces. Each such graphical user interface may be disposed at any appropriate location (e.g., on the powerhead; on a remote control). The first and second options may be selected in any appropriate manner. Representative ways of making a selection between the first and second options include without limitation by a keyboard, mouse, or touch screen display.

The second and third aspects may be used in combination. In the case of both the second aspect and the combination of the second and third aspects, the following may be employed individually or in combination: 1) the first syringe may be removed from the powerhead after the first syringe plunger driver has been at least partially retracted, while the second syringe may be removed from the powerhead after the second syringe plunger driver has been at least partially retracted; and 2) the first syringe plunger driver may be retracted to its first fully retracted position without stopping, and the second syringe plunger driver may be retracted to its second fully retracted position without stopping.

The initial retraction of each of the first and second syringe plunger drivers when utilized by the first, second, and third aspects may be initiated after the corresponding syringe plunger driver has reached a stopped position. This stopped position may correspond with a fully extended position (e.g., an end of a discharge stroke) or otherwise. Any retraction of a syringe plunger driver "toward" its corresponding fully retracted position in the case of each of the first, second, and third aspects encompasses stopping at one or more intermediate positions prior to reaching this fully retracted position.

The first and third aspects may also be used in combination. The following discussion, up to the start of the discussion of the fourth aspect of the present invention, pertains to the first aspect, as well as to the noted combination of the first and third aspects.

The retraction of the first syringe plunger driver to a first intermediate position may be done for any appropriate purpose. In one embodiment, this retraction of the first syringe plunger driver relieves a pressure within the first syringe. The second retraction of the second syringe plunger driver (a movement at least toward or in the direction of its second fully retracted position) may be initiated after the first syringe plunger driver has reached and been stopped at its first intermediate position. The retraction of the first syringe plunger driver to its first intermediate position and the retraction of the second syringe plunger driver at least toward or in the direction of its second fully retracted position may be initiated simultaneously, may occur simultaneously, or both.

The second syringe plunger driver may be retracted to its second fully retracted position without stopping. The second retraction of the second syringe plunger driver at least toward or in the direction of its second fully retracted position alternatively may entail retracting the second syringe plunger driver to a second intermediate position, where the second syringe plunger driver is then stopped. The retractions of the first and second syringe plunger drivers to their respective first and second intermediate positions may occur simultaneously, or sequentially and in any order. The first syringe may be removed after the first syringe plunger driver has reached its first intermediate position, the second syringe may be removed after the second syringe plunger driver has been at least partially retracted and including after it has reached its second intermediate position, or both. At least at some point in time after the second syringe plunger driver has been stopped at any second intermediate position, the second syringe plunger driver may be retracted to its second fully retracted position.

The first retraction may entail retracting the first syringe plunger driver a distance that corresponds with a fluid volume of no more than about 5 milliliters. Consider the case where the first syringe plunger driver is retracted from a first stopped position to a first intermediate position. If the first syringe plunger driver were to be extended from this first intermediate position to this first stopped position, the amount of fluid discharged from the first syringe would be no more than about 5 milliliters for the case of the above-noted embodiment. The retraction of the second syringe plunger driver to its second intermediate position may entail retracting the second syringe plunger driver a distance that corresponds with a fluid volume of no more than about 5 milliliters (e.g., between a second stopped position and a second intermediate position).

The first intermediate position and any second intermediate position each may be any appropriate location and each may be established on any appropriate basis. In one embodiment, the first and/or second intermediate positions may be at a fixed, constant location from the first and second fully retracted position, respectively. In one embodiment, the first and/or second intermediate positions may be based upon each of the first stopped position and the first fully retracted position, and the second stopped position and the second fully retracted position, respectively. In one embodiment, the location of the first and/or second intermediate position may be a fixed distance from the first and second stopped position, respectively, and regardless of the location of the first and second stopped position. For instance, the first intermediate position for the first syringe plunger driver may be a distance corresponding with 5 milliliters of fluid from a first stopped position for the first syringe plunger driver, whether the first stopped position is the first fully extended position of the first syringe plunger driver for purposes of a fluid delivery protocol, or whether the first stopped position corresponds with the position of the first syringe plunger driver when a fluid delivery protocol has been prematurely terminated. Similarly, the second intermediate position for the second syringe plunger driver may be a distance corresponding with 5 milliliters of fluid from a second stopped position for the second syringe plunger driver, whether the second stopped position is the second fully extended position of the second syringe plunger driver for purposes of a fluid delivery protocol, or whether the second stopped position corresponds with the position of the second syringe plunger driver when a fluid delivery protocol has been prematurely terminated.

The programmed retraction sequence may be initiated on any appropriate basis. In one embodiment, the programmed retraction sequence is initiated by a programmed input, by software, or both. In another embodiment, the programmed retraction sequence is initiated by user input.

A fluid delivery protocol (e.g., an injection protocol) may be executed for purposes of delivering a fluid to a fluid target (e.g., for injection into a patient). In the case of medical application, this protocol may be referred to as a medical fluid delivery protocol. In any case, this fluid delivery protocol may be in the form of a programmed fluid delivery sequence of one or more programmed parameters. Any appropriate fluid delivery protocol may be utilized. In one embodiment, the programmed retraction sequence is initiated after the fluid delivery protocol has been completed or has been prematurely terminated, and which may be determined in any appropriate manner.

Fourth and fifth aspects of the present invention are each embodied by a power injector. This power injector includes a powerhead, first and second syringes that are interconnected with the powerhead, first and second syringe plunger drivers that are at least interconnectable with the first and second syringes, respectively, and control logic. This control logic is configured to include a syringe plunger driver retraction protocol (hereafter a "retraction protocol"). In the case of the fourth aspect, this retraction protocol is configured to retract the first syringe plunger driver from a first stopped position to a first intermediate position that is somewhere between the first stopped position and a first fully retracted position, and to also retract the second syringe plunger driver from a second stopped position at least toward or in the direction of a second fully retracted position. In the case of the fifth aspect, this retraction protocol is configured to retract the first syringe plunger driver from a first stopped position at least toward or in the direction of a first fully retracted position, and to simultaneously retract the second syringe plunger driver from a second stopped position at least toward or in the direction of a second fully retracted position.

A sixth aspect of the present invention is embodied by a power injector. This power injector includes a powerhead, at least one syringe that is interconnected with the powerhead (hereafter a "first syringe"), at least one syringe plunger driver (hereafter a "first syringe plunger driver") that is at least interconnectable with its corresponding syringe, a graphical user interface, and control logic. This control logic is configured to include a syringe plunger driver retraction protocol (hereafter a "retraction protocol"), and is further configured to present first and second options on the graphical user interface. The first option is to enable an automatic initiation of the retraction protocol. The second option is to enable a manual initiation of the retraction protocol.

The features discussed above with regard to the graphical user interface and the selection of the first and second options for the case of the third aspect may be utilized (individually or in any combination) and/or are equally applicable to the sixth aspect. In one embodiment, the retraction protocol in the case of the sixth aspect may be configured to retract the first syringe plunger driver from a first stopped position at least toward or in the direction of a first fully retracted position, and to simultaneously retract the second syringe plunger driver from a second stopped position at least toward or in the direction of a second fully retracted position. For the case of the above-noted embodiment, as well as for the case of the fifth aspect of the present invention, the retraction protocol may be configured to retract the first syringe plunger driver from its first stopped position to its first fully retracted position without stopping, and to simultaneously retract the second syringe plunger driver from its second stopped position to its second fully retracted position without stopping.

The fourth and sixth aspects may also be used in combination. Unless otherwise noted, the following discussion pertains to the fourth aspect, as well as to the noted combination of the fourth and sixth aspects. Initially, the discussion presented above with regard to the first intermediate position for the first syringe plunger driver and any second intermediate position for the second syringe plunger driver is equally applicable to both the fourth aspect as well as to the combination of the fourth and sixth aspects (e.g., a partial retraction corresponding with a 5 milliliter "limit").

The retraction protocol may be configured such that the second syringe plunger driver is retracted at least toward or in the direction of its second fully retracted position after the first syringe plunger driver has been retracted from its first stopped position and to its first intermediate position, where the first syringe plunger driver is then stopped. The retraction protocol may also be configured such that an initiation of the retraction of the first syringe plunger driver from its first stopped position to its first intermediate position, and the initiation of the retraction of the second syringe plunger driver from its second stopped position at least toward or in the direction of its second fully retracted position, occurs on a simultaneous basis.

The retraction protocol may be configured such that the second syringe plunger driver is retracted from its second stopped position to its second fully retracted position without stopping. Alternatively, the retraction protocol may be configured such that the second syringe plunger driver is retracted from its second stopped position to a second intermediate position, where the second syringe plunger driver is then stopped. The retraction protocol may be configured such that the retractions of the first and second syringe plunger drivers to their respective first and second intermediate positions occur simultaneously, or sequentially, and in any order.

The programmed retraction sequence may be initiated on any appropriate basis. In one embodiment, the programmed retraction sequence is initiated by a programmed input, by software, or both. In another embodiment, the programmed retraction sequence is initiated by user input.

A fluid delivery protocol (e.g., an injection protocol) may be executed for purposes of delivering a fluid to a fluid target (e.g., for injection into a patient). In the case of medical application, this protocol may be referred to as a medical fluid delivery protocol. In any case, this fluid delivery protocol may be in the form of a programmed fluid delivery sequence of one or more programmed parameters. Any appropriate fluid delivery protocol may be utilized. In one embodiment, the programmed retraction sequence is initiated after the fluid delivery protocol has been completed or has been prematurely terminated.

The remainder of this Summary pertains to each of the first through the sixth aspects. The power injector may be of any appropriate size, shape, configuration, and/or type. The power injector may be used for any appropriate application where the delivery of one or more fluids is desired, including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between the power injector and one or more other components (e.g., scan delay information, injection start signal, injection rate).

Any appropriate number of syringes may be integrated with the power injector in any appropriate manner (e.g., detachably; front-loaded; side-loaded; rear-loaded (third aspect only)), any appropriate fluid may be discharged from a given syringe of the power injector (contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., to a patient). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

Any syringe plunger driver that is utilized may be of any appropriate size, shape, configuration, and/or type. Each such syringe plunger driver may be capable of at least bi-directional movement (e.g., a movement in a first direction for discharging fluid; a movement in a second direction for accommodating a loading of fluid or so as return to a position for a subsequent fluid discharge operation). Each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). In one embodiment, the syringe plunger driver is in the form of a ram that is threadably interconnected with a rotatable lead or drive screw. The following characterizations may be made in relation to each syringe that may be utilized, and these characterizations apply both individually or in any combination: 1) each syringe may be of any appropriate size, shape, configuration, size, and/or type; 2) each syringe may be interconnected with the powerhead in any appropriate manner; and 3) each syringe may interface with a syringe plunger driver in any appropriate manner.

DETAILED DESCRIPTION

Figure 1:
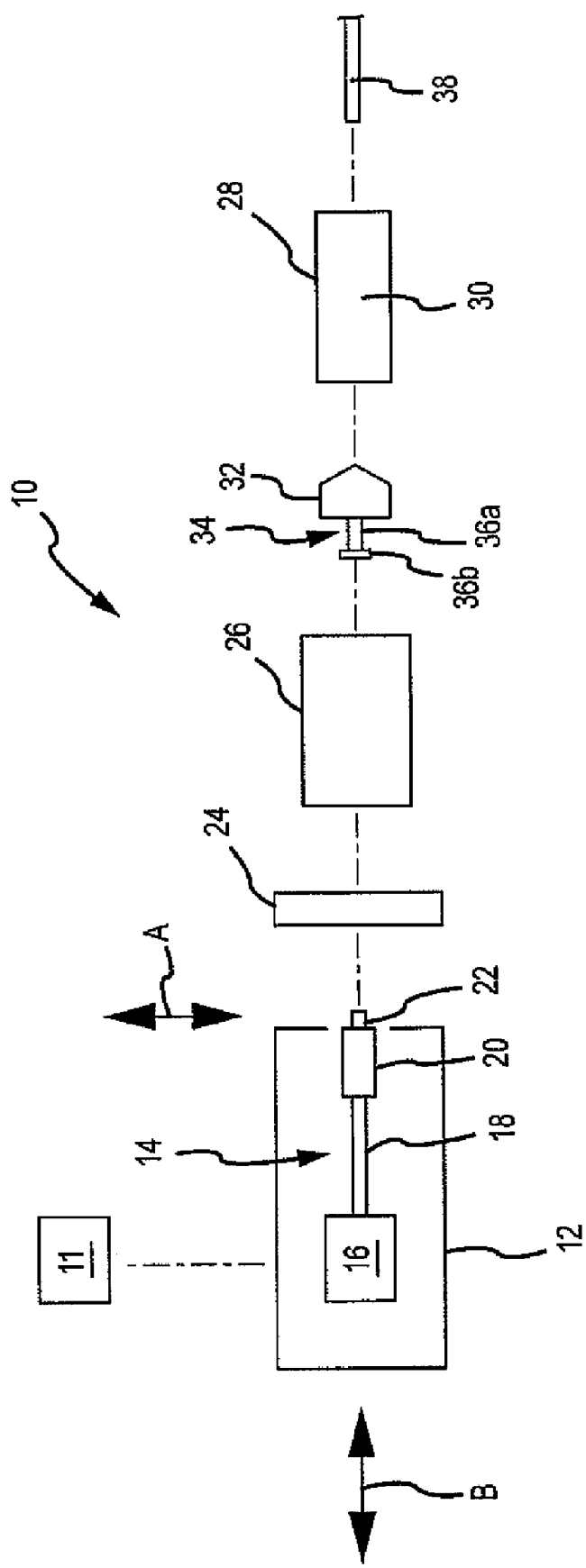
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically installed on the powerhead 12, followed by disposing the syringe 28 within the pressure jacket 26. The same pressure jacket 26 will typically remain installed on the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly 14 that interacts (e.g., interfaces) with the syringe 28 to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 may interact with each syringe plunger 32 of the power injector 10 in any appropriate manner (e.g., by mechanical contact; by an appropriate coupling (mechanical or otherwise)) so as to be able to move or advance the syringe plunger 32 in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be required. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
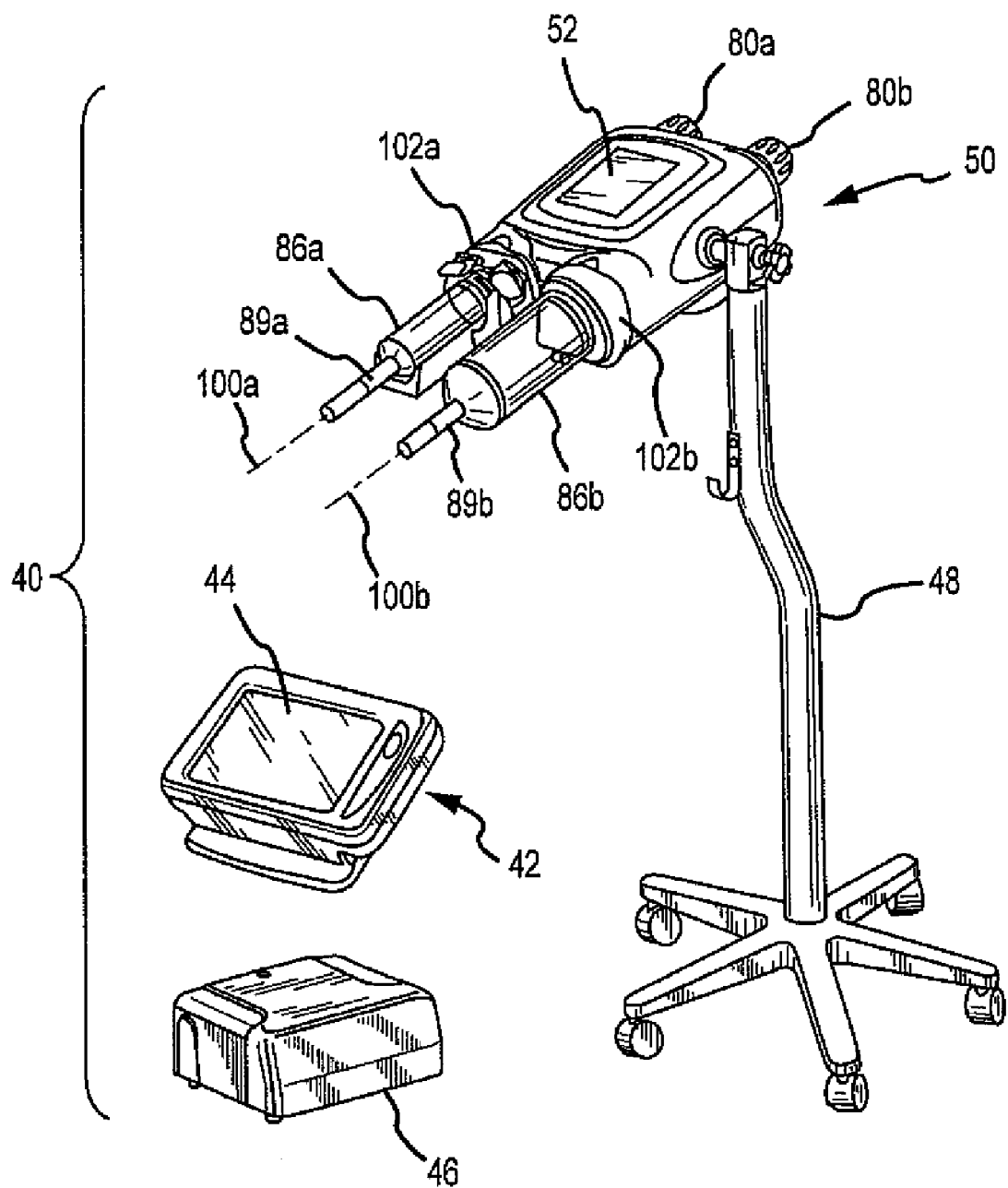
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
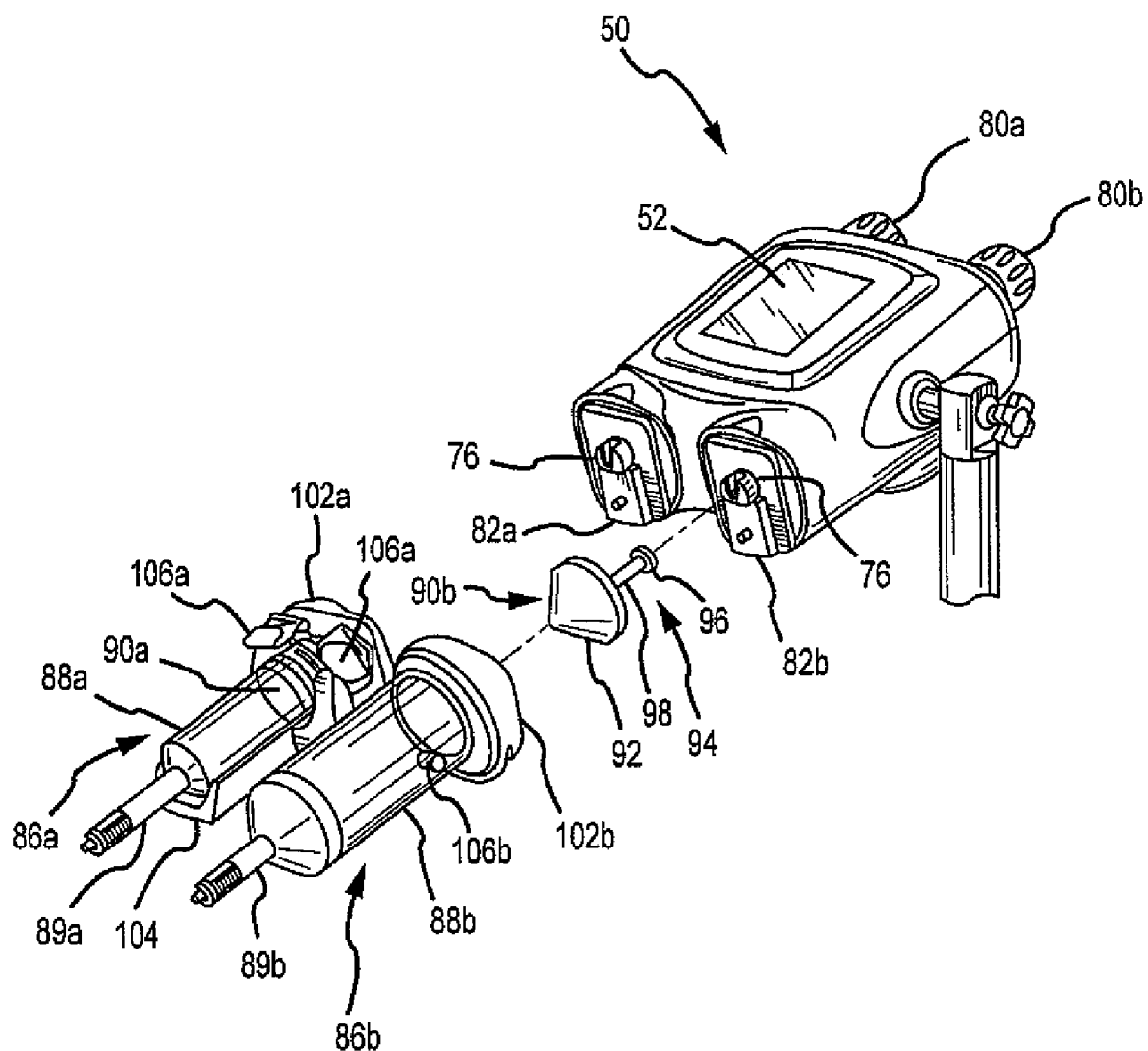
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within the syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74, which are each part of a syringe plunger drive assembly 56 for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74, which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 26, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
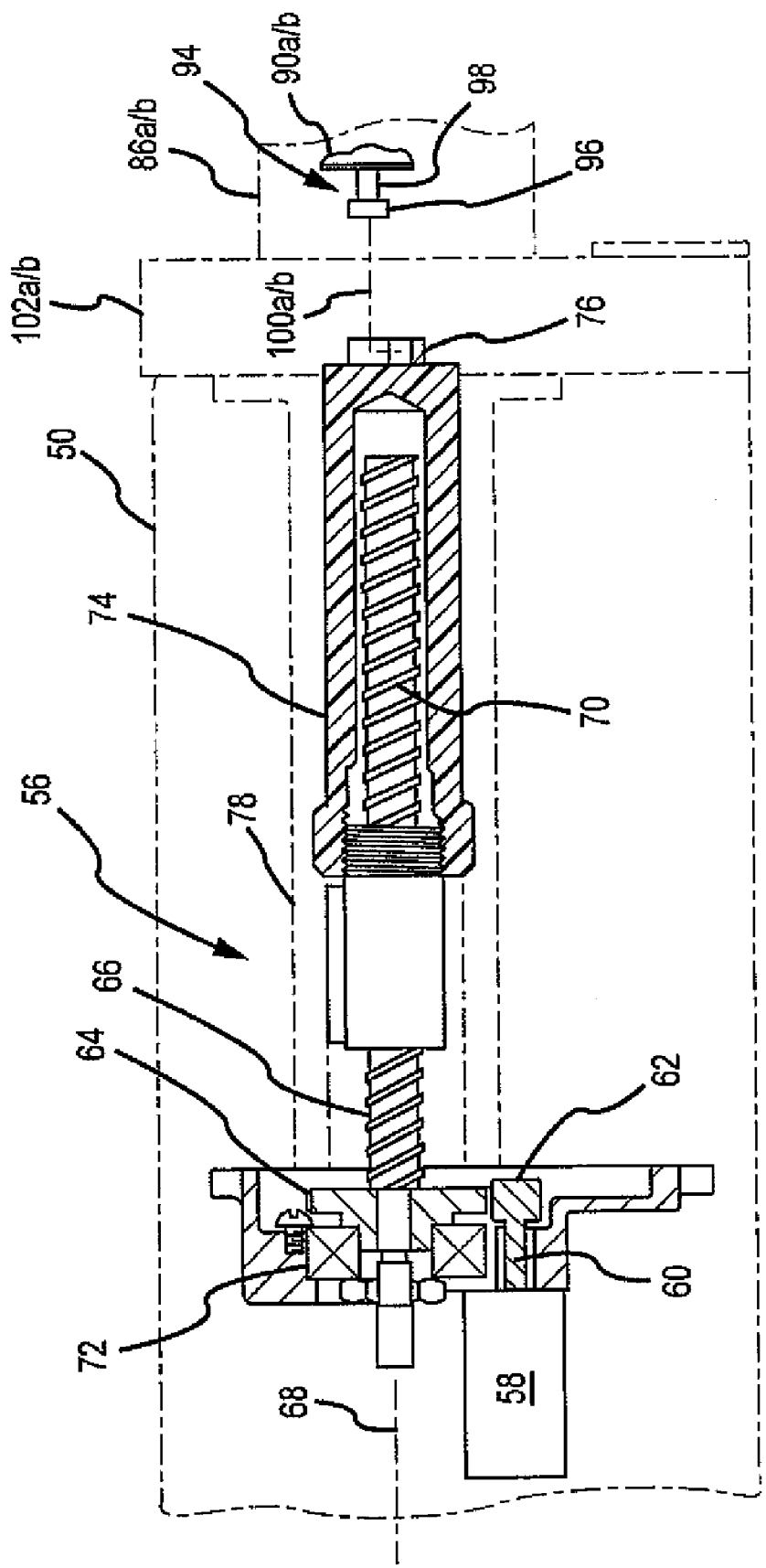
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

Figure 3:
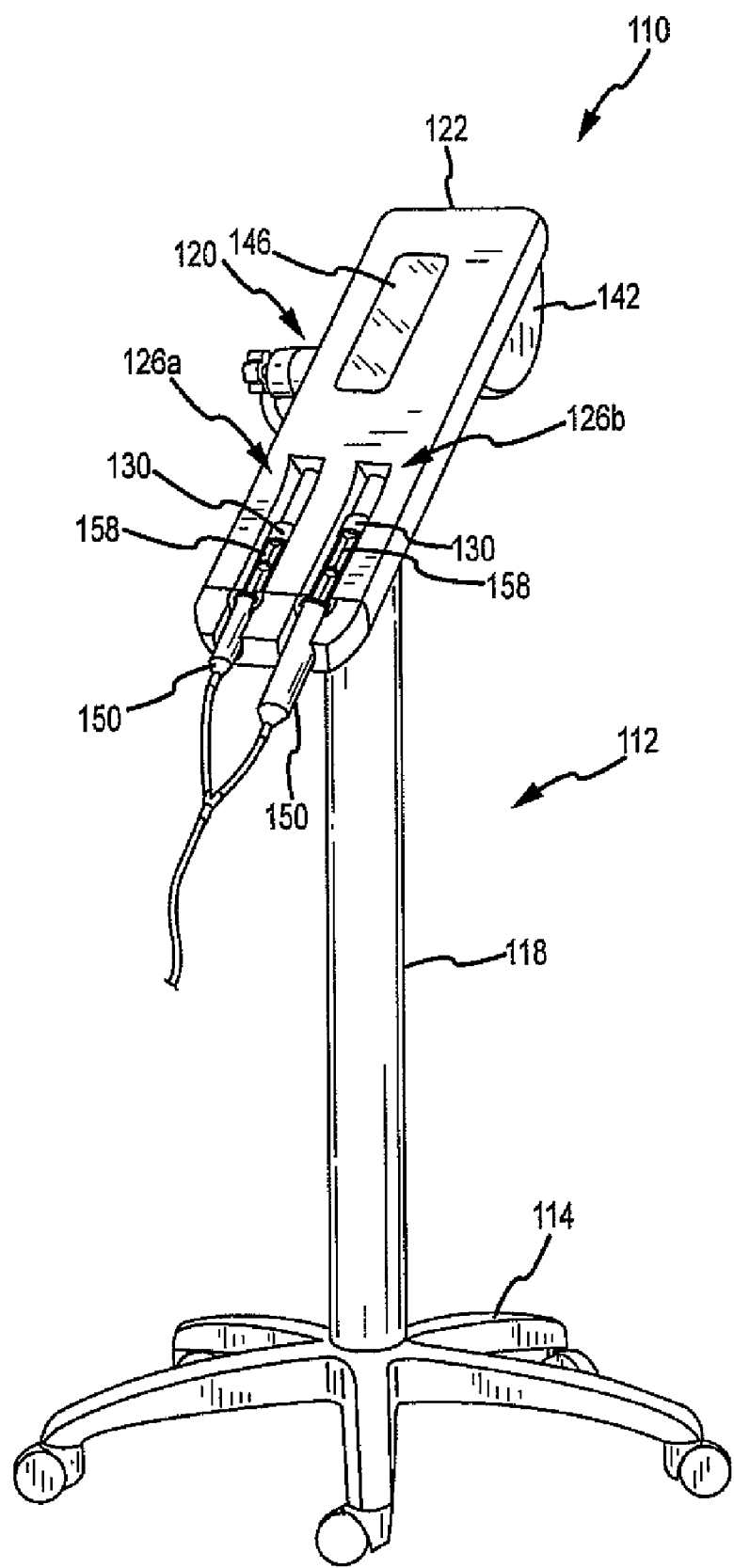
FIG. 3 is a perspective view of another embodiment of a portable, stand-mounted, dual-head power injector.

FIG. 3 is a perspective view of one embodiment of a power injector 110 that includes a support or stand 112, along with a powerhead 122 that is movably interconnected with the support 112 by a movable joint 120 (e.g., pivotally, for instance to accommodate the powerhead 122 being in one position to draw or otherwise load a fluid into one or more syringes 150, and to further accommodate the powerhead 122 being in another position for an injection procedure). The support 112 may be of any appropriate size, shape, configuration, and/or type. The support 112 of the illustrated embodiment is in the form of a movable or portable base 114 (e.g., having a plurality of casters, rollers, or the like for portability), along with a column 118 that extends at least generally upwardly from the base 114. It should be appreciated that the support 112 need not include transportability functionality in all instances. Other configurations may be appropriate for the support 112. For instance, the support 112 could be adapted so as to be mountable to an appropriate structure (e.g., a wall, ceiling, or floor), could be adapted so as to include one or more positional adjustability features, or both.

The powerhead 122 may include an appropriate display or user interface screen 146 to accommodate providing one or more operational inputs to the power injector 110, to display various information, or the like. One or more other data input devices of any appropriate type could be integrated with the powerhead 122 outside of the display 146 as well (e.g., a remote console). The powerhead 122 is of a dual-head configuration, and thereby incorporates a pair of what may be characterized as syringe drivers 126*a*, 126*b*. Further in this regard, the power injector 110 includes a syringe 150 for each of the syringe drivers 126*a*, 126*b*, where each syringe includes a plunger 158 that may be axially advanced to discharge fluid. Typically, these syringes 150 will be detachably interconnected with (e.g., mounted on) the powerhead 122 in any appropriate manner, although such need not always be the case. In the illustrated embodiment, the syringes 150 are "side loaded" by disposing each syringe 150 within an appropriately sized concave opening in the powerhead 122. As such, the power injector 110 may also be characterized as being of a side-loading type.

Each syringe 150 may be of any appropriate size, shape, configuration, and/or type. Although the syringes 150 discharge into common tubing in the illustrated embodiment, such need not always be the case. The power injector 110 may integrate the powerhead 122 and syringes 150 in any appropriate manner, including without limitation using pressure jackets or without using pressure jackets. The powerhead 122 could also be adapted to utilize any appropriate number of syringes 150, including without limitation a single syringe 150 (e.g., a single-head configuration).

Each syringe driver 126*a*, 126*b* includes a ram 130 that is threadably engaged with a corresponding drive screw (not shown, but contained within the powerhead housing). Rotation of a given drive screw axially advances its corresponding ram 130 along its long axis in a direction that is dictated by the rotational direction of the drive screw. The drive screws are rotated through an operative interconnection with a motor 142 of the power injector 110, where the motor 142 may be of any appropriate size, shape, configuration, and/or type (e.g., an electric motor, a hydraulic motor, pneumatic motor, a piezoelectric motor).

Axial movement of a given ram 130 in the direction of its corresponding syringe 150 provides for a fluid discharge from this syringe 150, while an axial movement of a given ram 130 away from its corresponding syringe 150 accommodates, for instance, loading or an introduction of an appropriate fluid into this syringe 150, a removal of the syringe 150, or both. The ram 130 may be coupled with a plunger 158 that is at least partially disposed within the syringe 150, such that movement of the ram 130 away from its corresponding syringe 150 retracts its associated plunger 158. In the embodiment of FIG. 3, however, the end of the ram 130 merely "butts up" against its corresponding syringe plunger 158. Therefore, advancing a ram 130 toward its corresponding syringe 150 in the FIG. 3 configuration will cause the ram 130 to engage its corresponding plunger 158 to advance the same for an injection. However, retracting the ram 130 will cause the same to disengage its corresponding plunger 158, for instance such that the corresponding syringe 150 may be removed from the powerhead 122.

The power injectors 10, 40, 110 of FIGS. 1, 2A-C, and 3 each may be used for any appropriate application, including without limitation for medical imaging applications where fluid is injected into a subject (e.g., a patient). Representative medical imaging applications for the power injectors 10, 40, 110 include without limitation computed tomography or CT imaging, magnetic resonance imaging or MRI, SPECT imaging, PET imaging, X-ray imaging, angiographic imaging, optical imaging, and ultrasound imaging. The power injectors 10, 40, 110 each could be used alone or in combination with one or more other components. The power injectors 10, 40, 110 each may be operatively interconnected with one or more components, for instance so that information may be conveyed between the power injector 10, 40, 110 and one or more other components (e.g., scan delay information, injection start signal, injection rate).

Any number of syringes may be utilized by each of the power injectors 10, 40, 110, including without limitation single-head configurations (for a single syringe) and dual-head configurations (for two syringes). In the case of a multiple syringe configuration, each power injector 10, 40, 110 may discharge fluid from the various syringes in any appropriate manner and according to any timing sequence (e.g., sequential discharges from two or more syringes, simultaneous discharges from two or more syringes, or any combination thereof). Each such syringe utilized by each of the power injectors 10, 40, 110 may include any appropriate fluid, for instance contrast media, a radiopharmaceutical, saline, and any combination thereof. Each such syringe utilized by each of the power injectors 10, 40, 110 may be installed in any appropriate manner (e.g., rear-loading configurations may be utilized; front-loading configurations may be utilized; side-loading configurations may be utilized).

Figure 4:
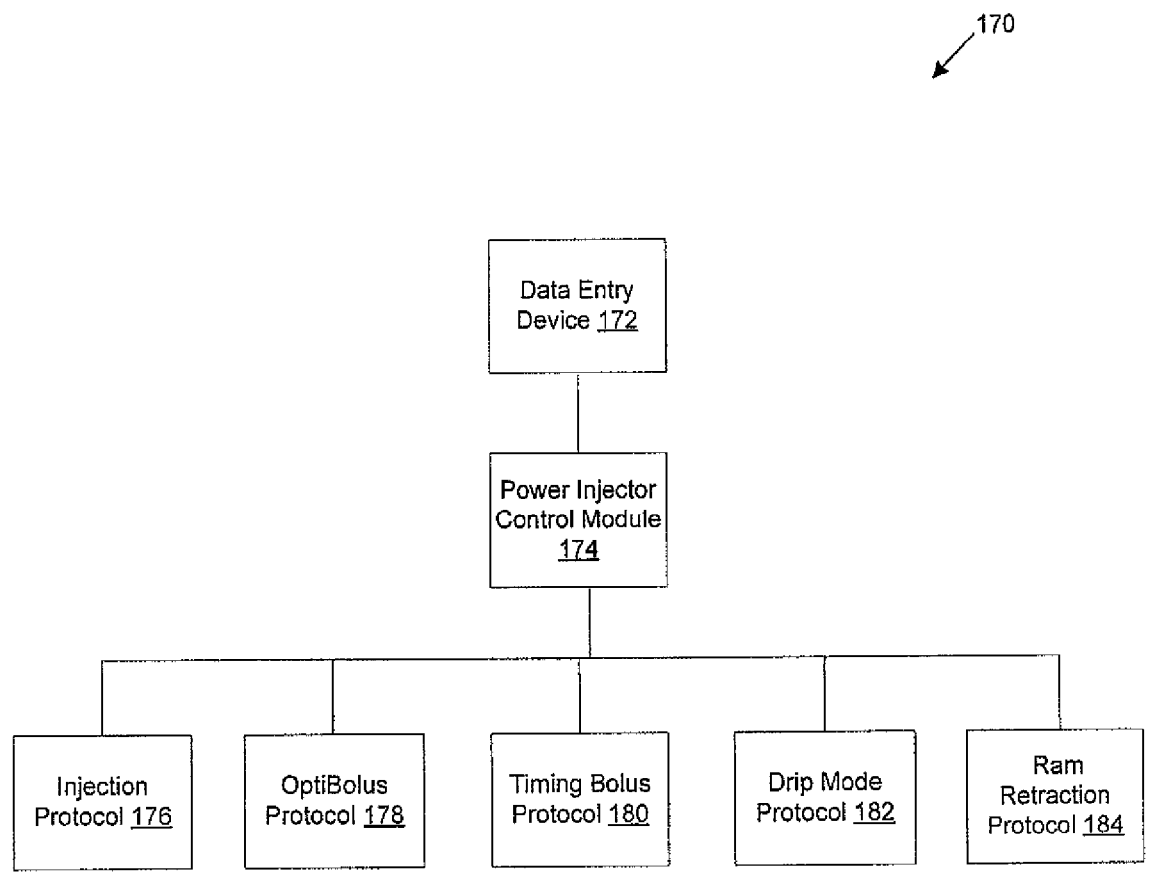
FIG. 4 is a schematic of one embodiment of a power injector control system.

FIG. 4 illustrates one embodiment of a power injector control system 170 that may be utilized by any appropriate power injector, including without limitation the power injector 10 of FIG. 1, the power injector 40 of FIGS. 2A-C, and the power injector 110 of FIG. 3. The power injector control system 170 may include one or more data entry devices 172 of any appropriate configuration and/or type (e.g., a keyboard, a mouse, a touch screen display, a soft key display, a touch pad, a track ball). One or more of these data entry devices 172 may be operatively interconnected with a power injector control logic or module 174. The power injector control module 174 may be of any appropriate form and/or configuration, may be implemented or integrated in any appropriate manner, or both (e.g., in the power injector software; implemented by software, hardware, firmware, and any combination thereof). In one embodiment, the functionality of the control logic 174 is provided by one or more processors of any appropriate size, shape, configuration, and/or type. In one embodiment, the functionality of the control logic 174 is provided by one or more computers.

The power injector control module 174 may be configured to include at least one fluid delivery or injection protocol 176 (e.g., for a medical application, and which may be referred to as a medical fluid delivery procedure or operation) and a ram retraction protocol 184, and each of which may be in the form of a programmed sequence. For a medical application, the protocol 176 may be referred to as a medical fluid delivery protocol 176. Each injection protocol 176 may be configured to control the manner in which one or more fluids are being delivered to a fluid target, such as by being injected into a patent. A particular injection protocol 176 may be configured to deliver a programmed volume of a first fluid at a programmed flow rate, as well as a programmed volume of a second fluid at a programmed flow rate. Each delivery of each of the first and second fluids may be characterized as a phase. One or more phases may be utilized for each of the first and second fluids. In one embodiment, the first fluid is contrast media and the second fluid is saline. The ram retraction protocol 184 will be discussed in more detail below, but generally is configured to control the manner in which each syringe plunger driver (e.g., a ram) is retracted, for instance after execution or upon completion of an injection protocol 176.

The power injector control module 174 of FIG. 4 may include one or more additional protocols as desired/required, and each of which may be in the form of a programmed sequence. Representative protocols that may be utilized by the power injector control module 174 as desired/required, in addition to at least one injection protocol 176 and a ram retraction protocol 184, include without limitation an Opti-Bolus® protocol 178, a Timing Bolus® protocol 180, and a drip mode protocol 182. Generally, the OptiBolus® protocol 178 may be configured to deliver an exponentially decaying flow rate injection that optimizes the contrast usage and provides an extended period of uniform enhancement of the area of interest. The Timing Bolus® injection protocol 180 may be configured to provide a timing bolus injection—a small volume of contrast media, followed by a small volume of saline—to a patient for purposes of determining the optimal scan delay needed to capture the contrast media in the area of interest. The drip mode protocol 182 may be configured to provide a drip injection—a low flow rate injection of a small volume of saline delivered to the patient to keep open the fluid pathway from the power injector to the patient.

Figure 5:
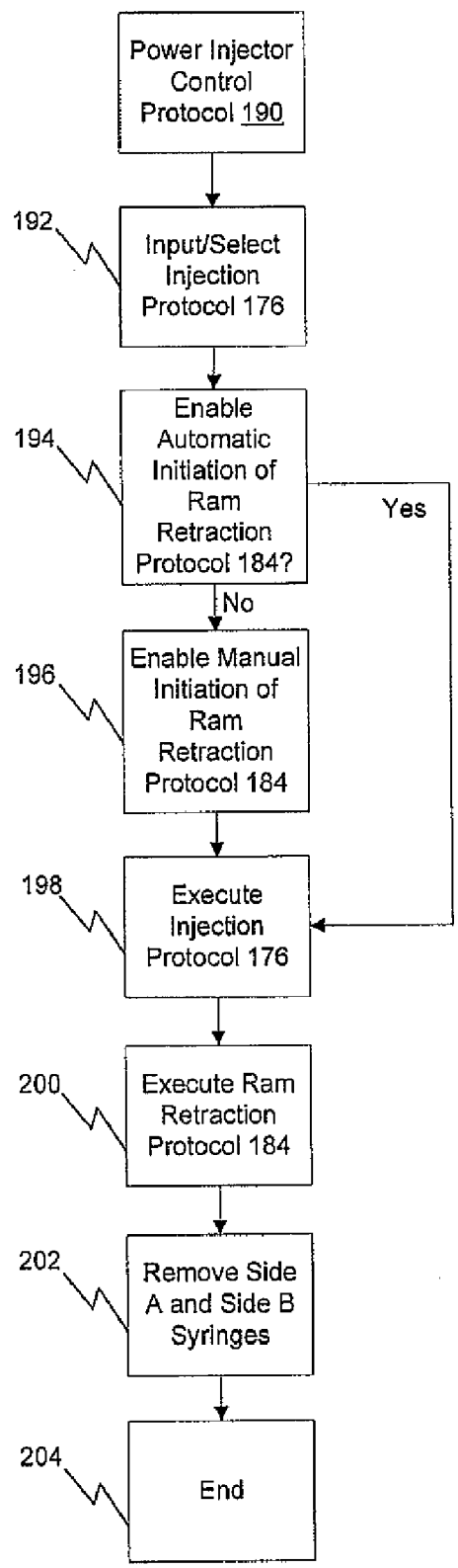
FIG. 5 is one embodiment of a power injector control protocol that may be used by the power injector control system of FIG. 4.

One embodiment of a power injector control protocol 190 is illustrated in FIG. 5, and may be utilized by the power injector control module 174 discussed above in relation to FIG. 4 to execute an injection protocol 176 and a ram retraction protocol 184. The power injector control protocol 190 is illustrated in relation to a dual-head power injector—a power injector having a pair of syringes and a corresponding syringe plunger driver or ram. Hereafter, such a power injector may be referred to as having an A side (e.g., one of the syringes and its corresponding syringe plunger driver or ram), as well as a B side (e.g., the other of the syringes and its corresponding syringe plunger driver or ram). Each of the A and B sides may contain any appropriate fluid (e.g., contrast media, a radiopharmaceutical, saline, and any combination thereof). It will be appreciated that the power injector control protocol 190 may be adapted for use with a power injector that utilizes any appropriate number of syringes.

The power injector control protocol 190 is configured to allow an injection protocol 176 to be input in any appropriate manner (e.g., via one or more data entry devices 172 (FIG. 4) or selected in any appropriate manner (e.g., via one or more data entry devices 172 (FIG. 4), for instance from a plurality of injection protocols 176 stored in memory and accessible through the power injector control protocol 190). The power injector control protocol 190 is configured to allow the ram retraction protocol 184 to be initiated on two different bases. An automatic initiation of the ram retraction protocol 184 may be initiated through execution of step 194 (e.g., via user input using a data entry device 172 (FIG. 4)). A manual initiation of the ram retraction protocol 184 may be initiated through execution of step 196 (e.g., via user input using a data entry device 172 (FIG. 4)). An option to enable an automatic initiation of the ram retraction protocol (step 194), or to enable a manual initiation of the ram retraction protocol 184 (step 194), may be presented to a user on one or more graphical user interfaces at any appropriate location (e.g., on a powerhead, on a remote control). It should be appreciated that steps 192, 194, and 196 may be executed in any appropriate manner and in any appropriate sequence.

Step 198 of the power injector protocol 190 of FIG. 5 is directed to executing the injection protocol 176 that was input or selected in step 192. The ram retraction protocol 184 is executed by step 200 of the power injector control protocol 190, and in accordance with step 194 or 196 (e.g., whichever option was previously enabled). In one embodiment, the ram retraction protocol 184 is initiated either automatically or manually only after the injection protocol 176 has been completed or terminated. However, the ram retraction protocol 184 could be initiated and executed at least in part during a continued execution of the injection protocol 176 (e.g., if the side A syringe plunger driver or ram has reached its fully extended position (e.g., the end of its discharge stroke), the ram retraction protocol 184 could be configured to initiate a retraction of the side A syringe plunger driver or ram even though the side B syringe plunger driver or ram has not yet reached its fully extended position (e.g., the end of its discharge stroke) pursuant to the injection protocol 176.

The side A and side B syringes may be removed from the powerhead of the power injector, in accordance with step 202 of the power injector control protocol 190, at any appropriate time after the injection protocol 176 has been completed or terminated. In one embodiment, the side A and side B syringes are removed only after their corresponding syringe plunger driver or ram has at least been partially retracted through execution of the ram retraction protocol 184 (step 200). The protocol 190 may return control to any appropriate portion of the power injector control module 174 (FIG. 4), for instance through execution of step 204.

Figure 6:
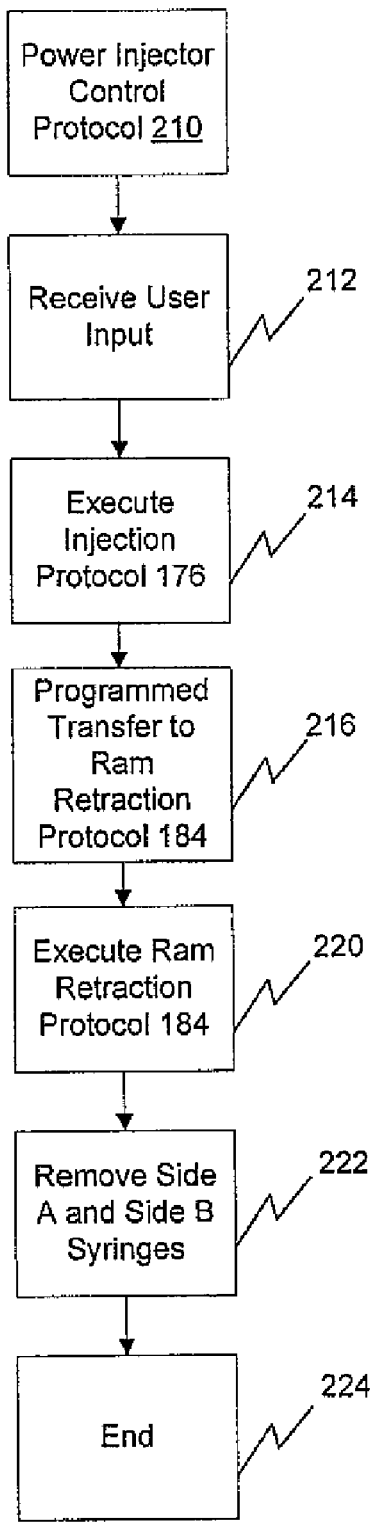
FIG. 6 is another embodiment of a power injector control protocol that may be used by the power injector control system of FIG. 4.

Another embodiment of a power injector control protocol 210 is illustrated in FIG. 6, and may be utilized by the power injector control module 174 discussed above in relation to FIG. 4 to execute an injection protocol 176 and a ram retraction protocol 184. The power injector control protocol 210 is illustrated in relation to a dual-head power injector—a power injector having a pair of syringes and a corresponding syringe plunger driver or ram. It will be appreciated that the power injector control protocol 210 may be adapted for use with a power injector that utilizes any appropriate number of syringes.

The power injector control protocol 210 may accommodate the provision of user input in any appropriate manner, for any appropriate purpose (e.g., for inputting/selecting a particular injection protocol 176) and in accordance with execution of step 212 of the protocol 210. User input may not be required in all instances. In any case, an injection protocol 176 is executed in accordance with step 214. A ram retraction protocol 184 is also executed. How the ram retraction protocol 184 is initiated is subject to a number of characterizations. One characterization is that there is a programmed transfer to the ram retraction protocol 184 and as reflected by step 216, and the ram retraction protocol 184 is thereafter executed through execution of step 220. Another characterization is that the power injector control protocol 210 may be configured to automatically execute the ram retraction protocol 184, versus in direct response to user input. Another characterization is that the configuration of the power injector control protocol 210 itself may transfer control to the ram retraction protocol 184.

The side A and side B syringes may be removed from the powerhead of the power injector, through execution of step 222 of the power injector control protocol 210, at any appropriate time after the injection protocol 176 has been completed or terminated. In one embodiment, the side A and side B syringes are removed only after their corresponding syringe plunger driver or ram has at least been partially retracted through execution of the ram retraction protocol 184 (step 220). The protocol 210 may return control to any appropriate portion of the power injector control module 174 (FIG. 4), for instance through execution of step 224.

The ram retraction protocol 184 discussed above in relation to the power injector control system 170 of FIG. 4, the power injector control protocol 190 of FIG. 5, and the power injector control protocol 210 of FIG. 6, may be of any appropriate configuration. FIGS. 7-10 illustrate various embodiments of this ram retraction protocol 184, and again which may be in the form of a programmed sequence. In one embodiment, each of these protocols may be initiated (e.g., automatically or manually) after the associated injection protocol 176 has been completed or terminated. However, at least certain of the ram retraction protocols of FIGS. 7-10 could be initiated and executed at least in part during a continued execution of the injection protocol 176 (e.g., if the side A syringe plunger driver or ram has reached its fully extended position (e.g., the end of its discharge stroke), a particular ram retraction protocol could be configured to initiate a retraction of the side A syringe plunger driver or ram even though the side B syringe plunger driver or ram has not yet reached its fully extended position (e.g., the end of its discharge stroke) pursuant to the injection protocol 176). The side-load configuration of the power injector 110 of FIG. 3 is particularly suited for the ram retraction protocols of FIGS. 7-10. As noted above and in the case of the power injector 110 of FIG. 3, the retraction of its rams 130 does not retract the corresponding syringe plunger 158. Therefore, once the rams 130 have been retracted at least a certain amount and have thereby become disengaged with the corresponding syringe plunger 158, the syringes 150 may be more readily removed.

Figure 7:
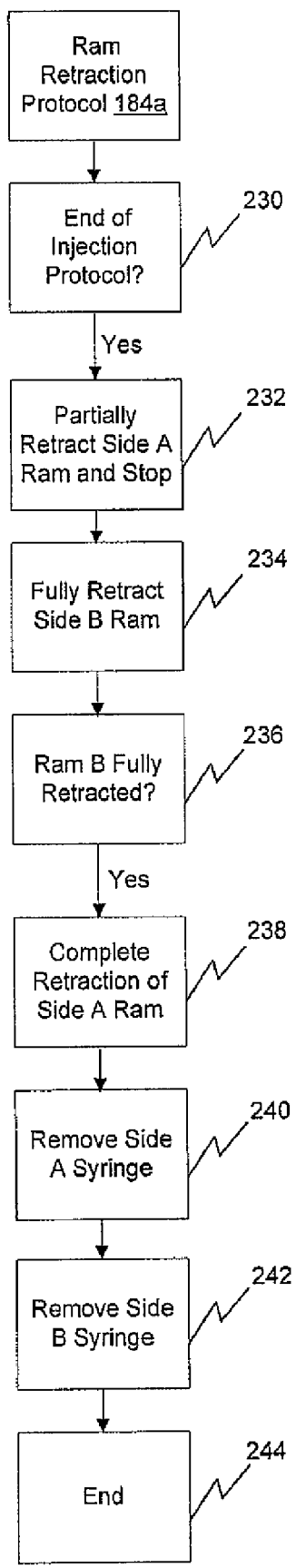
FIG. 7 is one embodiment of a ram retraction protocol that may be used by the power injector control system of FIG. 4, where one of the rams is only initially partially retracted.

The ram retraction protocol 184a of FIG. 7 may be configured to assess whether the associated fluid delivery or injection protocol has been completed or terminated through execution of step 230. However and in accordance with the foregoing, step 230 may not be required in all instances. Whether the ram retraction protocol 184a is automatically or manually initiated (e.g., in accordance with the power injector control protocol 190 of FIG. 5), the ram retraction protocol 184a retracts the side A syringe plunger driver or ram from a first stopped position (e.g., its fully extended position for purposes of the corresponding injection protocol) to a first intermediate position that is somewhere between this first stopped position and a first fully retracted position for the side A syringe plunger driver or ram. That is and in accordance with step 232, the side A syringe plunger driver or ram is partially retracted, and it may be partially retracted any appropriate amount/distance. In one embodiment, the partial retraction of the side A syringe plunger driver or ram corresponds with a fluid volume of no more than about 5 milliliters. For instance, if the side A syringe plunger driver or ram was advanced from the first intermediate position to the first stopped position, there would be a discharge of no more than about 5 milliliters from the first syringe in the case of the above-noted embodiment.

After the side A syringe plunger driver or ram has been partially retracted in accordance with step 232 of the ram retraction protocol 184a of FIG. 7, the side B syringe plunger driver or ram is fully retracted or is retracted from a second stopped position (e.g., its fully extended position for purposes of the corresponding injection protocol) to a second fully retracted position. Once the side B syringe plunger driver or ram has reached its second fully retracted position (and which may be determined in any appropriate manner for purposes of step 236 of the ram retraction protocol 184a), step 238 of the protocol 184a provides for a retraction of the side A syringe plunger driver or ram from its first intermediate position (associated with step 232) to its first fully retracted position.

The side A syringe may be removed at any appropriate time and in accordance with step 240 of the ram retraction protocol 184a of FIG. 7, and the side B syringe may be removed at any appropriate time and in accordance with step 242 of the ram retraction protocol 184a. The partial retraction of the side A syringe plunger driver or ram associated with step 232 may be executed to relieve pressure on the side A syringe such that it may be removed from the powerhead prior to the side A syringe plunger driver or ram having reached its first fully retracted position. Therefore, an operator may remove the side A syringe pursuant to step 240 any time after execution of step 232. An operator may remove the side B syringe pursuant to step 242 after the side B syringe plunger driver or ram has been retracted at least a certain distance from its second stopped position and in accordance with step 234. The protocol 184a may return control to any appropriate portion of the power injector control module 174 (FIG. 4), for instance through execution of step 244.

The configuration of the ram retraction protocol 184a of FIG. 7 is particularly suited for power injector configurations that do not allow for the simultaneous operation of both of its A and B sides, although the ram retraction protocol 184a may be used with any appropriate power injector. Some power injectors use a single motor and a single drive circuit to separately drive the A and B side syringe plunger drivers or rams. Other power injectors use a pair of motors, but only a single drive circuit, to separately drive the A and B side syringe plunger drivers or rams. It should be appreciated that the A and B sides of the power injector could be reversed for purposes of the ram retraction protocol 184*a*.

Figure 8:
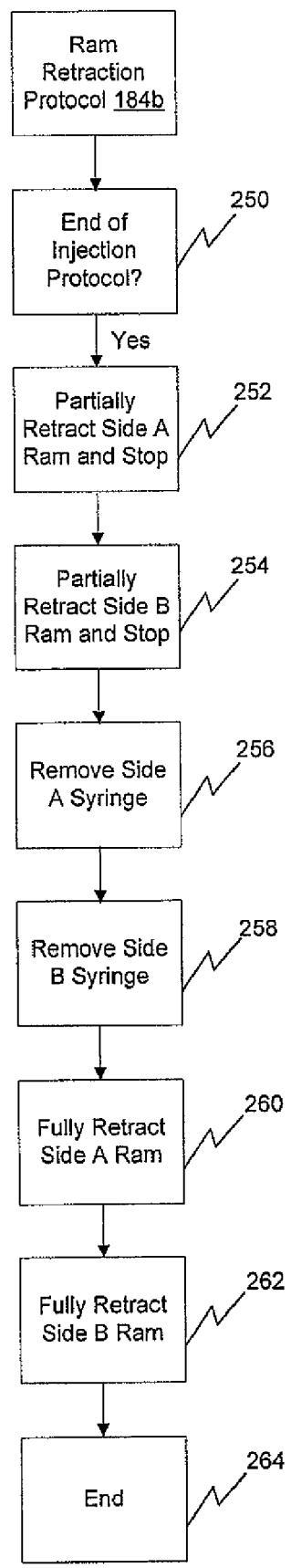
FIG. 8 is one embodiment of a ram retraction protocol that may be used by the power injector control system of FIG. 4, where both rams are only initially partially retracted and on a sequential basis.

The ram retraction protocol 184*b* of FIG. 8 may be configured to assess whether the associated fluid delivery or injection protocol has been completed or terminated through execution of step 250. However and in accordance with the foregoing, step 250 may not be required in all instances. Whether the ram retraction protocol 184*b* is automatically or manually initiated (e.g., in accordance with the power injector control protocol 190 of FIG. 5), the ram retraction protocol 184*b* retracts the side A syringe plunger driver or ram from a first stopped position (e.g., its fully extended position for purposes of the corresponding injection protocol) to a first intermediate position that is somewhere between this first stopped position and a first fully retracted position for the side A syringe plunger driver or ram. That is and in accordance with step 252, the side A syringe plunger driver or ram is partially retracted, and it may be partially retracted any appropriate amount/distance. However and in one embodiment, the partial retraction of the side A syringe plunger driver or ram may correspond with a fluid volume of no more than about 5 milliliters and in accordance with the foregoing.

The ram retraction protocol 184*b* of FIG. 8 retracts the side B syringe plunger driver or ram from a second stopped position (e.g., its fully extended position for purposes of the corresponding injection protocol) to a second intermediate position that is somewhere between this second stopped position and a second fully retracted position for the side B syringe plunger driver or ram. That is and in accordance with step 254, the side B syringe plunger driver or ram is partially retracted, and it may be partially retracted any appropriate amount/distance. However and in one embodiment, the partial retraction of the side B syringe plunger driver or ram may correspond with a fluid volume of no more than about 5 milliliters and in accordance with the foregoing. Although the side A and side B syringe plunger drivers or rams could be retracted the same amount/distance, such is not required.

The side A syringe may be removed at any appropriate time and in accordance with step 256 of the ram retraction protocol 184*b* of FIG. 8, and the side B syringe may be removed at any appropriate time and in accordance with step 258 of the ram retraction protocol 184*b*. The partial retraction of the side A syringe plunger driver or ram associated with step 252 may be executed to relieve pressure on the side A syringe such that it may be removed from the powerhead prior to the side A syringe plunger driver or ram having reached its first fully retracted position. Therefore, an operator may remove the side A syringe pursuant to step 256 any time after execution of step 252. Similarly, the partial retraction of the side B syringe plunger driver or ram associated with step 254 may be executed to relieve pressure on the side B syringe such that it may be removed from the powerhead prior to the side B syringe plunger driver or ram having reached its second fully retracted position. Therefore, an operator may remove the side B syringe pursuant to step 258 any time after execution of step 254.

Both the A and B side syringe plunger drivers or rams are returned to their respective fully retracted positions at some point in time after the partial retraction associated with steps 252 and 254. The ram retraction protocol 184*b* is configured to retract the side A syringe plunger driver or ram from its first intermediate position to its first fully retracted position (step 260). The ram retraction protocol 184*b* is also configured to retract the side B syringe plunger driver or ram from its second intermediate position to its second fully retracted position (step 262). Steps 260 and 262 may be executed in any order after each of steps 252 and 254 have been executed. The protocol 184*b* may return control to any appropriate portion of the power injector control module 174 (FIG. 4), for instance through execution of step 264.

The configuration of the ram retraction protocol 184*b* of FIG. 8 is particularly suited for power injector configurations that do not allow for the simultaneous operation of both of its A and B sides, although the ram retraction protocol 184*b* may be used with any appropriate power injector. Some power injectors use a single motor and a single drive circuit to separately drive the A and B side syringe plunger drivers or rams. Other power injectors use a pair of motors, but only a single drive circuit, to separately drive the A and B side syringe drivers or rams. In the illustrated embodiment: 1) the A side syringe plunger driver or ram is retracted (step 252); 2) after the A side syringe plunger driver or ram has reached and stopped at its first intermediate position, the B side syringe plunger driver or ram is retracted (step 254); 3) after the B side syringe plunger driver or ram has reached and stopped at its second intermediate position, the A side syringe plunger driver or ram is retracted to its first fully retracted position (step 260); and 4) after the A side syringe plunger driver or ram has reached and stopped at its first fully retracted position, the B side syringe plunger driver or ram is retracted to its second fully retracted position (step 262). It should be appreciated that steps 252 and 254 could be executed in any order (e.g., the B side syringe plunger driver or ram could be partially retracted before the A side syringe plunger driver or ram is partially retracted), and that steps 260 and 262 could be executed in any order (e.g., the B side syringe plunger driver or ram could be retracted from its second intermediate position to its second fully retracted position before the A side syringe plunger driver or ram is retracted from its first intermediate position to its first fully retracted position) and regardless of the order in which steps 252 and 254 were executed.

Figure 9:
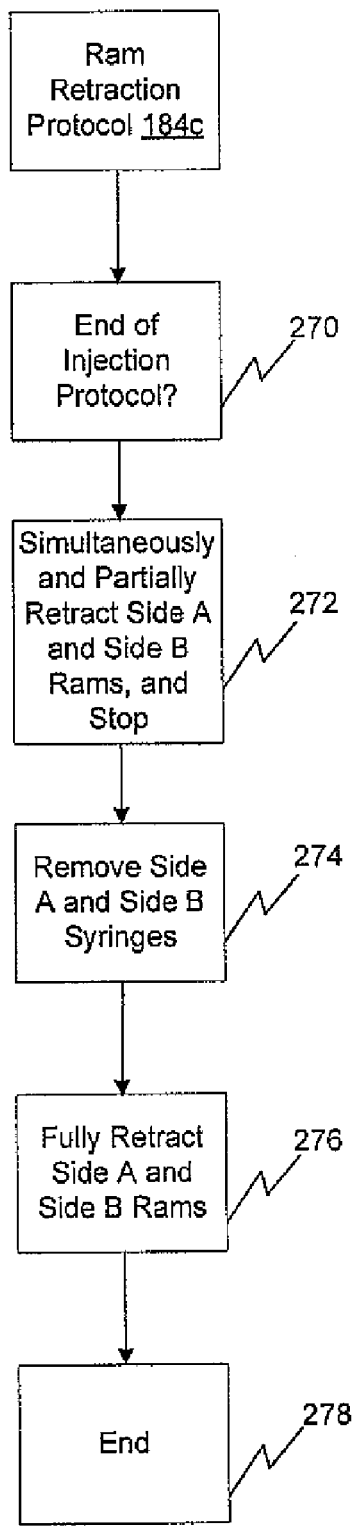
FIG. 9 is one embodiment of a ram retraction protocol that may be used by the power injector control system of FIG. 4, where both of the rams are only initially partially retracted and on a simultaneous basis.

The ram retraction protocol 184*c* of FIG. 9 may be configured to assess whether the associated fluid delivery or injection protocol has been completed or terminated through execution of step 270. However and in accordance with the foregoing, step 270 may not be required in all instances. Whether the ram retraction protocol 184*c* is automatically or manually initiated (e.g., in accordance with the power injector control protocol 190 of FIG. 5), the ram retraction protocol 184*c* retracts the side A syringe plunger driver or ram from a first stopped position (e.g., its fully extended position for purposes of the corresponding injection protocol) to a first intermediate position that is somewhere between this first stopped position and a first fully retracted position for the side A syringe plunger driver or ram, and simultaneously retracts the side B syringe plunger driver or ram from a second stopped position (e.g., its fully extended position for purposes of the corresponding injection protocol) to a second intermediate position that is somewhere between this second stopped position and a second fully retracted position for the side B syringe plunger driver or ram. That is and in accordance with step 272, the side A syringe plunger driver or ram and the side B syringe plunger driver or ram are each partially retracted and on a simultaneous basis, and each may be partially retracted any appropriate amount/distance. However and in one embodiment, the partial retraction of both the side A side B syringe plunger drivers or rams corresponds with a fluid volume of no more than about 5 milliliters and in accordance with the foregoing.

The side A syringe may be removed at any appropriate time and in accordance with step 274 of the ram retraction protocol 184c of FIG. 9, and the side B syringe may be removed at any appropriate time and in accordance with step 276 of the ram retraction protocol 184c. The partial retraction of the side A and B syringe plunger drivers or rams associated with step 272 may be executed to relieve pressure on the side A and B syringes such that they may be removed from the powerhead. Therefore, an operator may remove the side A and B syringes pursuant to step 274 any time after the execution of step 272.

Both the A and B side syringe plunger drivers or rams are returned to their respective fully retracted positions at some point in time after the partial retraction associated with step 272. In the illustrated embodiment, the ram retraction protocol 184c is configured to retract the side A syringe plunger driver or ram from its first intermediate position to its first fully retracted position and to retract the side B syringe plunger driver or ram from its second intermediate position to its second fully retracted position (step 276) after the expiration of a predetermined/programmed amount of time from when the side A and B syringe plunger drivers or rams have stopped at their respective first and second intermediate positions (step 272). The protocol 184b may return control to any appropriate portion of the power injector control module 174 (FIG. 4), for instance through execution of step 278.

Figure 10:
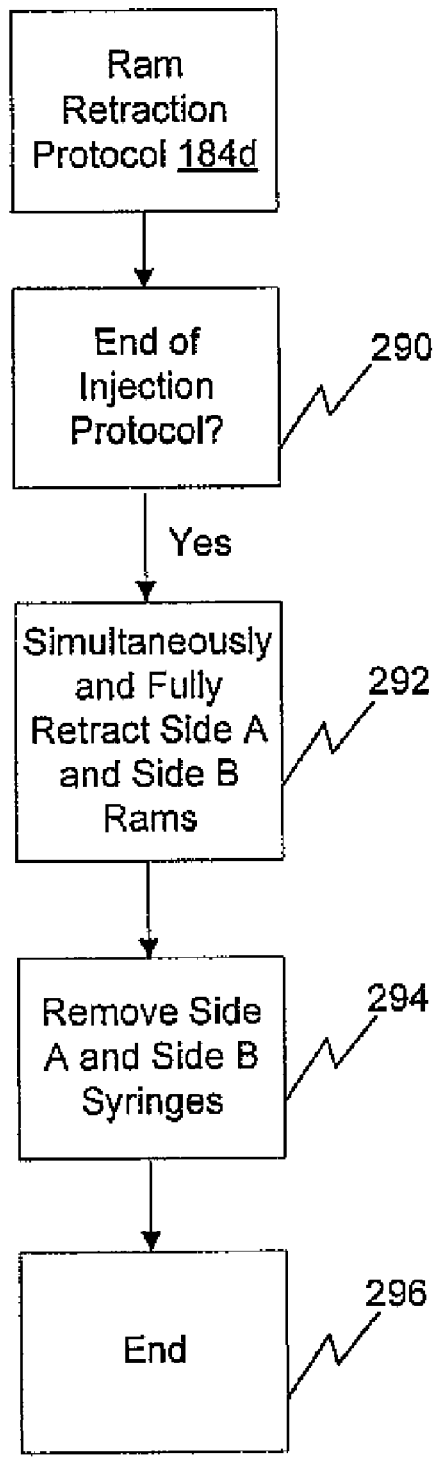
FIG. 10 is one embodiment of a ram retraction protocol that may be used by the power injector control system of FIG. 4, where both of the rams are simultaneously retracted to a fully retracted position.

The ram retraction protocol 184d of FIG. 10 may be configured to assess whether the associated fluid delivery injection protocol has been completed or terminated through execution of step 290. However and in accordance with the foregoing, step 290 may not be required in all instances. Whether the ram retraction protocol 184d is automatically or manually initiated (e.g., in accordance with the power injector control protocol 190 of FIG. 5), a simultaneous retraction of the side A and side B syringe plunger drivers or rams is initiated by step 292. That is, the ram retraction protocol 184d retracts the side A syringe plunger driver or ram from a first stopped position (e.g., its fully extended position for purposes of the corresponding injection protocol) to a first fully retracted position, and simultaneously retracts the side B syringe plunger driver or ram from a second stopped position (e.g., its fully extended position for purposes of the corresponding injection protocol) to a second fully retracted position. That is and in accordance with step 292, the side A syringe plunger driver or ram and the side B syringe plunger driver or ram are each fully retracted and on a simultaneous basis.

How step 292 of the ram retraction protocol 184d is initiated is subject to a number of characterizations. One characterization is that there is a programmed transfer to step 292. Another characterization is that the ram retraction protocol 184d may be configured to automatically execute step 292 (e.g., a programmed input), versus in direct response to user input. Another characterization is that the configuration of the ram retraction protocol 184d itself may transfer control to step 292. Another characterization is that step 292 is part of a programmed sequence. Yet another characterization is that step 292 is not initiated in direct response to user/operator input.

The side A and side B syringes may be removed at any appropriate time after the simultaneous retraction of the side A and side B syringe plunger drivers or rams has been initiated, and in accordance with step 294 of the ram retraction protocol 184d of FIG. 10. The protocol 184d may return control to any appropriate portion of the power injector control module 174 (FIG. 4), for instance through execution of step 296.

A number of points may be made in relation to each of the ram retraction protocols 184a-d of FIGS. 7-10. One is that each of these protocols 184a-d: 1) may be part of the power injector control logic or module 174 of FIG. 4; 2) may be used in each of the power injector control protocols 190, 210 of FIGS. 5 and 6, respectively, and 3) may define a programmed sequence at least in relation to the above-noted steps directed to retracting a syringe plunger driver or ram. The ram retraction protocol 184a of FIG. 7 includes at least steps 232, 234, 236, and 238 as a programmed sequence. The ram retraction protocol 184b of FIG. 8 includes at least steps 262, 254, 260, and 262 as a programmed sequence. The ram retraction protocol 184c of FIG. 9 includes at least steps 272 and 276 as a programmed sequence. The ram retraction protocol 184d of FIG. 10 includes at least step 292 as a programmed sequence.

The removal of syringes in accordance with each of the above-noted ram retraction protocols 184a-d of FIGS. 7-10 may be entirely automated in any appropriate manner, or stated another way the actual syringe removal operation(s) could be part of a programmed sequence. Another option is to exclude from any programmed sequence utilized by any of the ram retraction protocols 184a-d, each step directed to removing syringes—the actual removal of each syringe would not be part of a programmed sequence in this instance. Each syringe could thereby be removed entirely by hand or manually. At least one or more aspects, that at least somehow relate to the removal of each syringe discussed above in relation to the ram retraction protocols 184a-d, may be included as part of a programmed sequence (e.g., issuing a prompt or the like on a graphical user interface that it is now okay to manually remove the syringes; monitoring the "installed" status of the syringes—indicating whether or not a syringe is still installed on the powerhead).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector, comprising:
   a powerhead;
   first and second syringes interconnected with said powerhead;
   first and second syringe plunger drivers that are at least interconnectable with said first and second syringes, respectively; and
   control logic that comprises a syringe plunger driver retraction protocol, wherein said syringe plunger driver retraction protocol is executable in preparation for removal of said first and second syringes from said powerhead, wherein said syringe plunger driver retraction protocol is in the form of a programmed sequence within said control logic, and wherein said syringe plunger driver retraction protocol is configured to: a) retract said first syringe plunger driver from a first stopped position toward a first fully retracted position, but stops said first syringe plunger driver at a first intermediate position that is between said first stopped position and said first fully retracted position; b) retract said second syringe plunger driver from a second stopped position back to a second fully retracted position; and c) retract said first syringe plunger driver from said first intermediate position back to said first fully retracted position.

2. The power injector of claim 1, wherein a distance between said first stopped position and said first intermediate position corresponds with a fluid volume of no more than about 5 milliliters.

3. The power injector of claim 1, wherein said syringe plunger driver retraction protocol is configured to: a) retract said first syringe plunger driver from said first stopped position to said first intermediate position; b) thereafter retract said second syringe plunger driver from said second stopped position either back to a second intermediate position that is between said second stopped position and said second fully retracted position where said second syringe plunger driver is stopped, or all the way back to said second fully retracted position where said second syringe plunger driver is stopped.

4. The power injector of claim 1, wherein said syringe plunger driver retraction protocol is configured to: a) initiate a retraction of said first syringe plunger driver from said first stopped position to said first intermediate position; and b) simultaneously initiate a retraction of said second syringe plunger driver from said second stopped position either back to a second intermediate position that is between said second stopped position and said second fully retracted position where said second syringe plunger driver is stopped, or all the way back to said second fully retracted position where said second syringe plunger driver is stopped.

5. The power injector of claim 1, wherein said syringe plunger driver retraction protocol is configured to retract said second syringe plunger driver from said second stopped position to a second intermediate position that is between said second stopped position and said second fully retracted position, wherein said second syringe plunger driver is stopped at said second intermediate position.

6. The power injector of claim 5, wherein a distance between said second stopped position and said second intermediate position corresponds with a fluid volume of no more than about 5 milliliters.

7. The power injector of claim 5, wherein said syringe plunger driver retraction protocol is configured to: a) retract said first syringe plunger driver from said first stopped position to said first intermediate position; and b) thereafter retract said second syringe plunger driver from said second stopped position to said second intermediate position.

8. The power injector of claim 5, wherein said syringe plunger driver retraction protocol is configured to: a) initiate a retraction of said first syringe plunger driver from said first stopped position to said first intermediate position; and b) simultaneously initiate a retraction of said second syringe plunger driver from said second stopped position to said second intermediate position.

9. The power injector of claim 1, wherein said syringe plunger driver retraction protocol is configured to retract said second syringe plunger driver from said second stopped position to said second fully retracted position without stopping.

10. The power injector of claim 1, wherein said first and second syringes are interconnected with said powerhead when execution of said syringe plunger driver refraction protocol is initiated.

11. The power injector of claim 1, wherein said first syringe is removable from said powerhead after said first syringe plunger driver has been retracted to said first intermediate position through execution of said syringe plunger driver retraction protocol.

12. A power injector, comprising:
a powerhead;
first and second syringes interconnected with said powerhead;
first and second syringe plunger drivers that are at least interconnectable with said first and second syringes, respectively; and
control logic that comprises a syringe plunger driver retraction protocol, wherein said syringe plunger driver retraction protocol is executable in preparation for removal of said first and second syringes from said powerhead, wherein said syringe plunger driver retraction protocol is in the form of a programmed sequence within said control logic, and wherein said syringe plunger driver retraction protocol is configured to: a) retract said first syringe plunger driver from a first stopped position back toward a first fully retracted position, but stops said first syringe plunger driver at a first intermediate position that is between said first stopped position and said first fully retracted position; and b) simultaneously retract said second syringe plunger driver from a second stopped position back toward a second fully retracted position, but stops said second syringe plunger driver at a second intermediate position that is between said second stopped position and said second fully retracted position.

13. The power injector of claim 12, wherein said syringe plunger driver retraction protocol is configured to retract said first syringe plunger driver from said first intermediate position back to said first fully retracted position, and wherein said syringe plunger driver retraction protocol is configured to retract said second syringe plunger driver from said second intermediate position back to said second fully retracted position.

14. The power injector of claim 12, wherein said first and second syringes are removable from said powerhead after said first and second syringe plunger drivers have been retracted to said first and second intermediate positions, respectively, through execution of said syringe plunger driver retraction protocol.

15. The power injector of claim 12, wherein said syringe plunger driver retraction protocol is further configured to: c) retract said first syringe plunger driver from said first intermediate position back to said first fully retracted position; and d) retract said second syringe plunger driver from said second intermediate position back to said second fully retracted position.

16. A power injector, comprising:
a powerhead;
a first syringe interconnected with said powerhead;
a first syringe plunger driver that is at least interconnectable with said first syringe;
a graphical user interface; and
control logic that comprises a syringe plunger driver retraction protocol, wherein said syringe plunger driver retraction protocol is executable in preparation for removal of said first syringe from said powerhead, wherein said syringe plunger driver retraction protocol is in the form of a programmed sequence within said control logic, wherein said control logic is configured to present first and second options on said graphical user interface, wherein said first option is to enable automatic initiation of said syringe plunger driver retraction protocol, and wherein said second option is to enable manual initiation of said syringe plunger driver retraction protocol via user input.

17. The power injector of claim 16, wherein said power injector comprises a second syringe interconnected with said powerhead and a second syringe plunger driver that is at least interconnectable with said second syringe, wherein said syringe plunger driver retraction protocol is configured to: a) retract said first syringe plunger driver from a first stopped position back toward a first fully retracted position; and b) simultaneously retract said second syringe plunger driver from a second stopped position back toward a second fully retracted position.

18. The power injector of claim 17, wherein said syringe plunger driver retraction protocol is configured to: a) retract said first syringe plunger driver from said first stopped position back to said first fully retracted position without stopping; and b) simultaneously retract said second syringe plunger driver from said second stopped position back to said second fully retracted position without stopping.

19. The power injector of claim 16, wherein said power injector comprises a second syringe interconnected with said powerhead and a second syringe plunger driver that is at least interconnectable with said second syringe, wherein said syringe plunger driver retraction protocol is configured to: a) retract said first syringe plunger driver from a first stopped position back toward a first fully retracted position, but stops said first syringe plunger driver at a first intermediate position that is between said first stopped position and said first fully retracted position; and b) retract said second syringe plunger driver from a second stopped position back toward a second fully retracted position.

* * * * *